US00PP28604P2

(12) United States Plant Patent
Klemm et al.

(10) Patent No.: US PP28,604 P2
(45) Date of Patent: Nov. 7, 2017

(54) ***DIANTHUS* PLANT NAMED 'KLEDP15179'**

(50) Latin Name: *Dianthus caryophyllus*
Varietal Denomination: KLEDP15179

(71) Applicant: Klemm+Sohn GmbH & Co. KG, Stuttgart (DE)

(72) Inventors: Nils Klemm, Stuttgart (DE); Lena Gutbrodt, Bempfingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 2 days.

(21) Appl. No.: 14/999,100

(22) Filed: Mar. 30, 2016

(51) Int. Cl.
*A01H 5/02* (2006.01)

(52) U.S. Cl.
USPC ..... Plt./277

(58) Field of Classification Search
USPC ..... Plt./263.1, 272, 273, 177
See application file for complete search history.

*Primary Examiner* — Susan McCormick Ewoldt
*Assistant Examiner* — Karen Redden
(74) *Attorney, Agent, or Firm* — Bethany R. Roahrig; James M. Weatherly; Cochran Freund & Young, LLC

(57) ABSTRACT

A new *dianthus* plant particularly distinguished by having salmon colored flowers, good branching, and medium vigor, is disclosed.

1 Drawing Sheet

Genus and species: *Dianthus caryophyllus*.
Variety denomination: 'KLEDP15179'.

BACKGROUND OF THE NEW PLANT

The present invention comprises a new and distinct variety of *dianthus*, botanically known as *Dianthus caryophyllus* and hereinafter referred to by the variety name 'KLEDP15179'. 'KLEDP15179' resulted from a whole plant mutation of 'DCP-2010-1006' (unpatented) identified in March 2010 in Stuttgart, Germany.

In July of 2010 'KLEDP15179' was first vegetatively propagated by stem cuttings. 'KLEDP15179' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Salmon colored flowers;
2. Good branching; and
3. Medium vigor.

DESCRIPTION OF THE PHOTOGRAPH

This new *Dianthus* plant is illustrated by the accompanying photograph which shows an overall view of the plant. The colors shown are as true as can be reasonably obtained by conventional photographic procedures. The photograph is of a plant that is 12 weeks-old grown in a greenhouse in Stuttgart, Germany in April 2014.

DESCRIPTION OF THE NEW VARIETY

The following detailed descriptions set forth the distinctive characteristics of 'KLEDP15179'. The data which define these characteristics were collected from asexual reproductions carried out in Stuttgart, Germany. Data was collected on 6 month-old plants grown in a glass greenhouse in Stuttgart, Germany in March 2016. Color references are to The R.H.S. Colour Chart of The Royal Horticultural Society of London (R.H.S.), 5$^{th}$ edition (2007).

Classification:
- *Family*.—Caryophyllaceae.
- *Species*.—*Dianthus caryophyllus*.
- *Common name*.—Pot carnation.
- *Variety*.—'KLEDP15179'.

Parentage: Mutation of 'DCP-2010-1006' (unpatented).

Propagation:
- *Type*.—Stem cuttings.
- *Time to produce a rooted young plant*.—14 to 16 days.
- *Root description*.—White, fine.
- *Rooting habit*.—Lanceolate.

Plant description:
- *Plant form*.—Potted plant, upright.
- *Plant height*.—13.0 cm to 15.0 cm.
- *Plant diameter or spread*.—16.0 cm to 20.0 cm.

Lateral branches:
- *Length*.—8.0 cm to 10.0 cm.
- *Diameter*.—0.3 cm to 0.5 cm.
- *Internode length*.—2.0 cm to 3.0 cm.
- *Node length*.—0.3 cm to 0.4 cm.
- *Node diameter*.—0.4 cm.
- *Texture*.—Smooth.
- *Color*.—RHS 137A.
- *Branch*.—Solid.

Foliage description:
- *Arrangement*.—Opposite.
- *Length*.—4.0 cm to 6.0 cm.
- *Width*.—0.6 cm to 0.8 cm.
- *Shape*.—Lanceolate.
- *Apex*.—Acute.
- *Base*.—Obtuse.
- *Margin*.—Entire.
- *Texture (both surfaces)*.—Smooth.
- *Venation pattern*.—Palmate.

*Color*.—Immature leaves: Upper surface: RHS 143A. Lower surface: RHS 144A. Mature leaves: Upper surfaces: RHS 139A. Lower surface: RHS 137A. Venation: RHS 139A.

Flower description:

*Flower type and habit*.—Round, double, small sprays.

*Fragrance*.—Present.

*Natural flowering season*.—Spring to fall.

*Position of flowers relative to the foliage*.—Slightly above.

*Number of flowers per spray*.—3 to 4.

*Flower longevity*.—10 to 14 days.

*Flower buds*.—Length: 2.0 cm. Diameter: 0.8 cm to 1.0 cm. Shape: Elliptic. Color: RHS 137C and RHS 144A. Extrusion of the styles at bud stage: Absent.

*Corolla*.—Quantity of petals/arrangement: Approximately 15, arranged in several whorls. Corolla height: 1.5 cm to 2.0 cm. Petal length: 3.0 cm. Petal width: 1.5 cm to 2.0 cm. Petal shape: Spoon shaped. Petal apex: Obtuse. Petal base: Acute. Petal margin: Crenate. Depth of petal margin: Medium. Petal texture (both surfaces): Smooth. Petal color immature: Upper surface: RHS 52B. Lower surface: RHS 52D. Petal color mature: Upper surface: RHS 51B. Lower surface: RHS 51D. Calyx: Quantity of sepals/arrangement: 5, fused. Shape: Campanulate. Calyx height: 1.8 cm to 2.0 cm. Calyx diameter, at the apex: 0.8 cm to 1.0 cm. Sepal texture (both surfaces): Smooth. Sepal color: Upper surface: RHS 137A. Lower surface: RHS 137D.

Peduncles:

*Length*.—10.0 cm to 14.0 cm.

*Diameter*.—0.2 cm.

*Strength*.—Moderate.

*Texture*.—Smooth.

*Color*.—RHS 137A.

Reproductive organs:

*Stamens*.—Filament length: 0.4 cm to 0.6 cm. Filament color: RHS 155B. Anther length: 0.1 cm. Anther diameter: 0.05 cm. Anther color: RHS 19B. Pollen amount: Abundant.

*Pistils*.—Quantity: 1. Pistil length: 0.1 cm. Style length: 1.6 cm to 1.8 cm. Style color: RHS 56D. Stigma shape: Filamentous. Stigma color: RHS 55A. Ovary size: 0.4 cm to 0.6 cm. Ovary shape: Oval. Ovary color: RHS 144B and RHS 145B.

Fruit and seed: Seed sometimes observed.

Disease and insect/pest resistance: No special observations were made.

COMPARISON WITH PARENTAL LINE AND KNOWN VARIETY

'KLEDP15179' is a distinct variety of *dianthus*. 'KLEDP15179' is distinguished from its parent as described in Table 1:

TABLE 1

Comparison with Parental Line

| Trait | Variety 'KLEDP15179' | Parent 'DCP-2010-1006' |
|---|---|---|
| Flower color | Salmon | Red |

'KLEDP15179' is most similar to the commercial *dianthus* plant named 'Oscar' also known as 'KLEDP07089' (unpatented). Differences between the two varieties are described in Table 2:

TABLE 2

Comparison with Similar Variety

| Trait | Variety 'KLEDP15179' | Commercial line 'Oscar' |
|---|---|---|
| Flower color | Salmon | Pink with Purple eye |

We claim:

1. A new and distinct variety of *dianthus* plant named 'KLEDP15179' as illustrated and described herein.

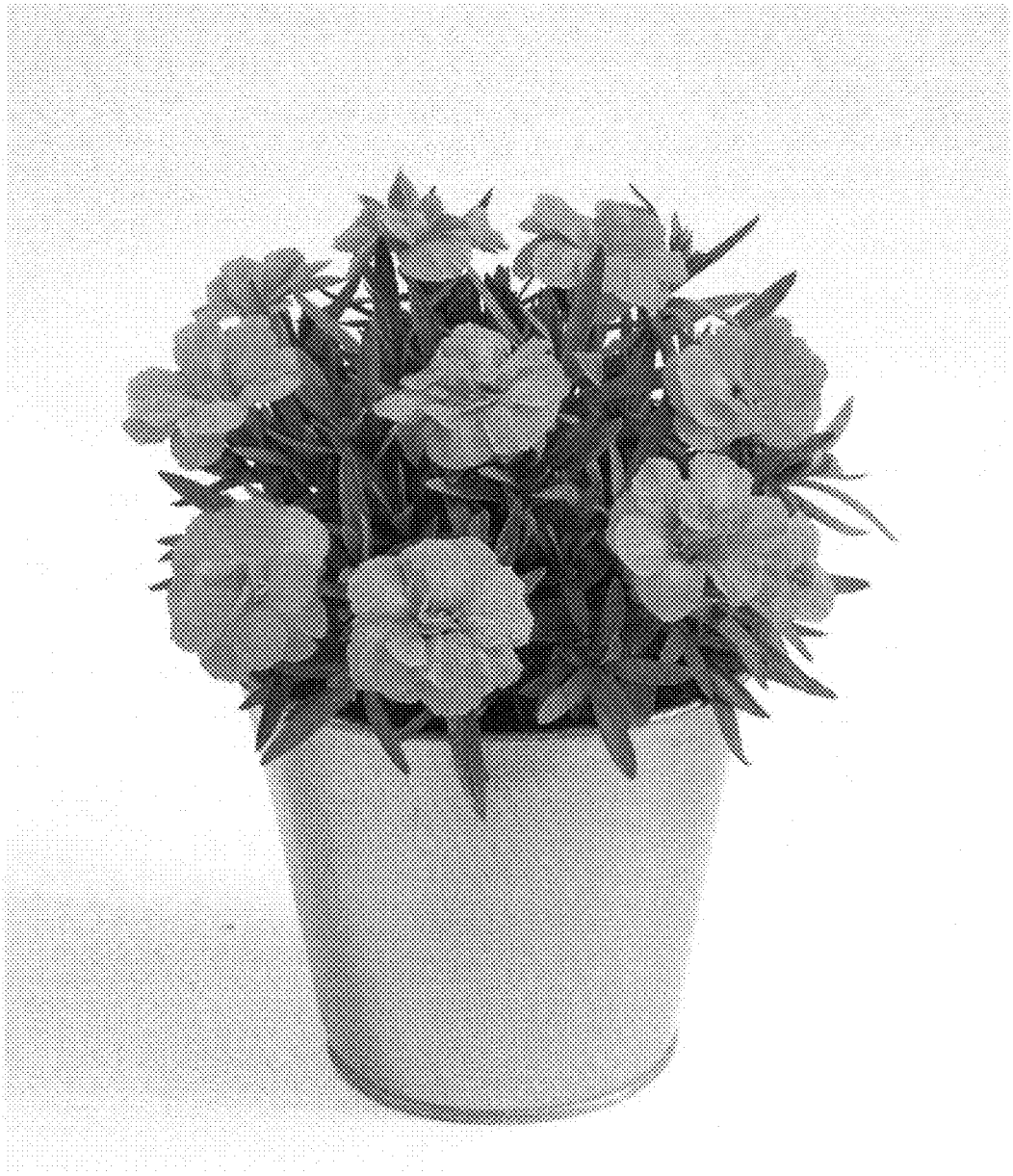

* * * * *